United States Patent [19]

Shoesmith, deceased et al.

[11] Patent Number: Plant 6,531

[45] Date of Patent: Jan. 10, 1989

[54] CHRYSANTHEMUM PLANT NAMED CRUSADER

[75] Inventors: Leonard H. Shoesmith, deceased, late of Westfield, England, by May V. Shoesmith, executrix; Peter S. Hesse, Bradenton, Fla.

[73] Assignee: Ball Pan Am Plant Company, Parrish, Fla.

[21] Appl. No.: 55,603

[22] Filed: May 29, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Crusader, characterized by its lavender ray floret color; single flower form; cushion growth habit; 8 week flowering response; and its ability to perform well in outdoor and pot mum programs.

1 Drawing Sheet

The present invention comprises a new and distinct cultivar of Chrysanthemum, botanically known as *Chrysanthemum morifolium,* Ramat., and referred to by the cultivar name Crusader.

Crusader is a product of a planned breeding program which had the objective of creating new chrysanthemum cultivars with cushion growth habit, relatively fast flower response, daisy type flower form, and having the ability for growing in pot or outdoor garden programs. Such traits in combination were not present in previously available commercial cultivars.

Crusader was originated from a hybridization made by Leonard H. Shoesmith in a controlled breeding program in 1980 in Westfield, Woking, England. Both the male and female parents of Crusader are unknown at this time. Crusader was discovered and selected as one flowering plant within the progeny of the stated parentage by Peter S. Hesse in November 1981 in a controlled environment in Parrish, Fla.

The first act of asexual reproduction of Crusader was accomplished when vegetative cuttings were taken from the initial selection in February 1982 in a controlled environment in Parrish, Fla. by a technician working under formulations established and supervised by Peter S. Hesse. Horticultural examination of selected units initiated in April 1982 has demonstrated that the combination of characteristics as herein disclosed for Crusader are firmly fixed and are retained through successive generations of asexual reproduction.

Crusader has not been observed under all possible environmental conditions. The phenotype may vary significantly with variations in environment such as temperature, light intensity, and day length. The following observations, measurements and comparisons describe plants grown in Parrish, Fla. under greenhouse conditions which approximate those generally used in commercial practice.

The following traits have been repeatedly observed and are determined to be basic characteristics of Crusader, which in combination distinguish this Chrysanthemum as a new and distinct cultivar:

1. Medium lavender ray floret color.
2. Daisy (single) flower type.
3. Fully expanded individual ray florets are 15–22 mm long and 4–6 mm wide.
4. Capitulum is 35–45 mm in diameter.

5. Average of 24 ray florets per capitulum.
6. Flowers 8 weeks after the onset of long days.
7. Performs well in the outdoor garden.
8. Can be produced well in 4½" up to 1 gallon containers.
9. Cushion growth habit.

Of the many commercial cultivars known to the present inventors, the most similar in comparison to Crusader is Stardom, disclosed in U.S. Plant Pat. No. 3,530. In comparison to Stardom, Crusader has a darker lavender flower color and is more fade resistant. Also, Crusader has an 8 week flower response compared to the 7 week flower response of Stardom. Both cultivars have a daisy (single) flower form and a cushion growth habit.

The accompanying photographic drawing shows typical inflorescence and foliage characteristics of Crusader. The photograph is in black and white, with several flowers being colored to accurately depict true flower color.

In the following description, color references are made to The Royal Horticultural Society Colour Chart. The color values were determined between 1:00 and 1:30 p.m. on May 14, 1987 under fluorescent lighting at Parish, Fla.

Classification:

*Botanical.*—*Chrysanthemum morifolium,* Ramat., cv. Crusader.

*Commercial.*—Garden mum of greenhouse pot.

INFLORESCENCE

A. Capitulum:

*Form.*—Flat.

*Type.*—Single.

*Diameter across face.*—35–45 mm.

B. Corolla of ray florets:

*Color (general tonality from a distance of three meters).*—Medium lavender.

*Color (upper surface).*—72B.

*Color (under surface).*—63C.

C. Corolla of disc florets:

*Color (mature).*—Yellow, typical disc floret color.

*Color (immature).*—Yellow green, also typical.

D. Reproductive organs:

*Androecium.*—Present in disc florets only.

*Gynoecium.*—Present in both ray florets and disc florets.

PLANT

A. General appearance:

*Height.*—17–20 cm when grown in a 4½" pot; height can vary upon growing conditions, growth regulator applications and other cultural practices.

B. Foliage:

*Color (upper surface).*—147A.

*Color (under surface).*—147B.

*Shape.*—Ovate with cleft margins.

We claim:

1. A new and distinct cultivar of Chrysanthemum plant named Crusader, as illustrated and described, and particularly characterized by its lavender ray floret color; single flower form; cushion growth habit; 8 week flowering response; and its ability to perform well in outdoor and pot mum programs.

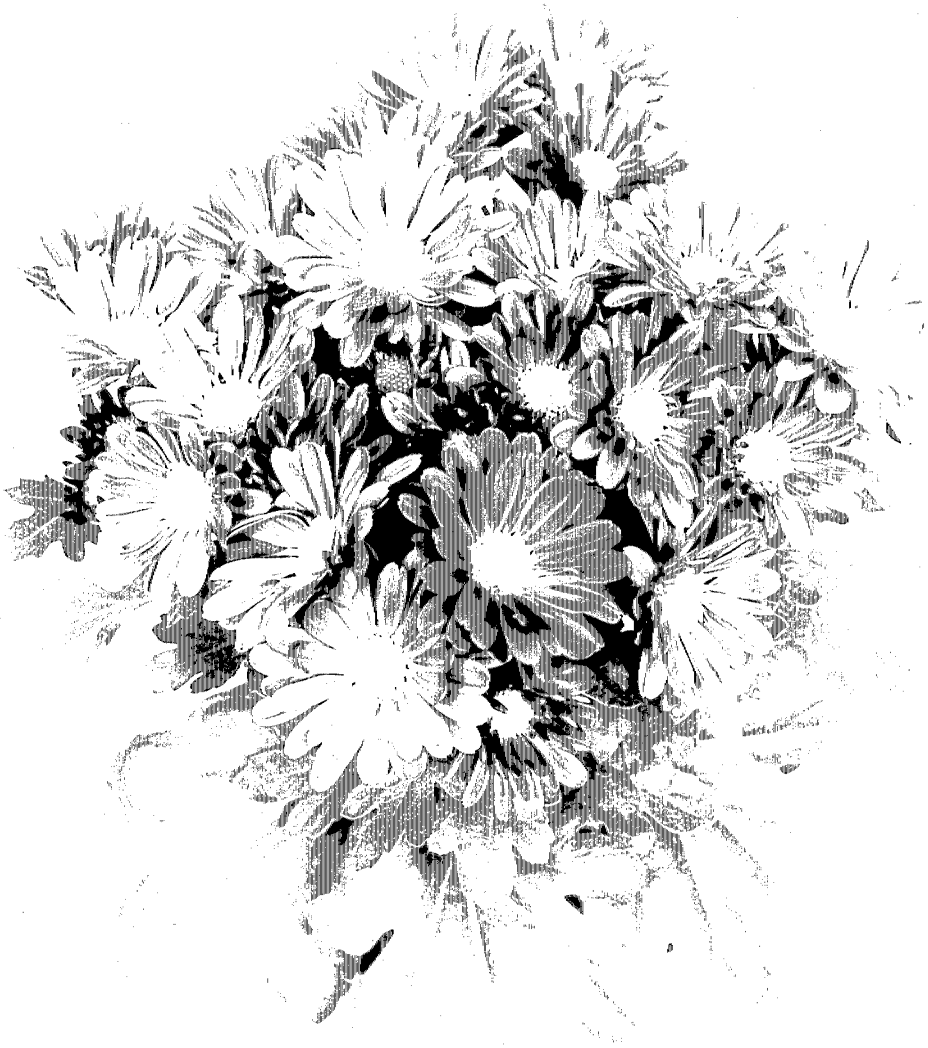

* * * * *